US00RE46062E

(19) United States
(12) Reissued Patent
James et al.

(10) Patent Number: US RE46,062 E
(45) Date of Reissued Patent: Jul. 12, 2016

(54) FLOW GUIDE

(71) Applicant: Endoguard Limited, Bury St. Edmunds, Suffolk (GB)

(72) Inventors: Adam Graham James, London (GB); Jie Chen, Sidcup (GB); Anthony Arthur Wills, London (GB)

(73) Assignee: Endoguard Limited (GB)

(21) Appl. No.: 14/688,150

(22) Filed: Apr. 16, 2015

Related U.S. Patent Documents

Reissue of:
(64) Patent No.: 8,419,624
Issued: Apr. 16, 2013
Appl. No.: 12/902,570
Filed: Oct. 12, 2010

(30) Foreign Application Priority Data

Oct. 12, 2009 (GB) ..... 0917857.5

(51) Int. Cl.
*A61B 1/12* (2006.01)
*A61B 1/00* (2006.01)

(52) U.S. Cl.
CPC *A61B 1/126* (2013.01); *A61B 1/127* (2013.01)

(58) Field of Classification Search
CPC ..... A61B 1/126; A61B 1/127
USPC ..... 600/157, 169, 175
See application file for complete search history.

(56) References Cited

U.S. PATENT DOCUMENTS 3,835,842 A 9/1974 Iglesias
4,576,146 A 3/1986 Kawazoe et al.
4,633,855 A 1/1987 Baba
4,667,656 A 5/1987 Yabe
4,770,163 A 9/1988 Ono et al.
5,125,394 A 6/1992 Chatenever et al.
5,167,220 A 12/1992 Brown
5,201,908 A 4/1993 Jones
5,207,213 A 5/1993 Auhll et al.
5,217,001 A 6/1993 Nakao et al.
5,237,984 A 8/1993 Williams, III et al.
5,313,934 A 5/1994 Wiita et al.
5,339,800 A 8/1994 Wiita et al.
5,348,555 A 9/1994 Zinnanti
5,392,766 A 2/1995 Masterson et al.
5,402,768 A 4/1995 Adair
5,413,092 A 5/1995 Williams, III et al.

(Continued)

FOREIGN PATENT DOCUMENTS

CA 2582352 9/2007
CN 1486666 4/2004

(Continued)

OTHER PUBLICATIONS

Vision Sciences, "ENT Slide-On EndoSheath System," 2007, one page.

(Continued)

*Primary Examiner* — Beverly M Flanagan
(74) *Attorney, Agent, or Firm* — Price Heneveld LLP

(57) ABSTRACT

A flow guide directs a fluid flow across a surface of a device, for example a lens surface of an endoscope, in a controlled manner to facilitate flow attachment to the surface. Embodiments include features that impart a non-uniform velocity profile and/or include guide surfaces for facilitating flow attachment and/or coverage.

28 Claims, 8 Drawing Sheets

(56) References Cited

U.S. PATENT DOCUMENTS

| | | | | |
|---|---|---|---|---|
| 5,419,309 | A | 5/1995 | Biehl | |
| 5,483,951 | A | 1/1996 | Frassica et al. | |
| 5,514,084 | A | 5/1996 | Fisher | |
| 5,518,502 | A | 5/1996 | Kaplan et al. | |
| 5,575,756 | A | 11/1996 | Karasawa et al. | |
| 5,637,075 | A | 6/1997 | Kikawada | |
| 5,651,757 | A | 7/1997 | Meckstroth | |
| 5,685,823 | A * | 11/1997 | Ito et al. | 600/127 |
| 5,725,477 | A * | 3/1998 | Yasui et al. | 600/127 |
| 5,725,478 | A | 3/1998 | Saad | |
| 5,894,369 | A | 4/1999 | Akiba et al. | |
| 6,110,103 | A | 8/2000 | Donofrio | |
| 6,126,592 | A | 10/2000 | Proch et al. | |
| 6,231,596 | B1 | 5/2001 | Collins | |
| 6,309,347 | B1 | 10/2001 | Takahashi et al. | |
| 6,409,657 | B1 * | 6/2002 | Kawano | 600/157 |
| 6,416,462 | B1 | 7/2002 | Tovey et al. | |
| 6,447,446 | B1 | 9/2002 | Smith et al. | |
| 6,695,773 | B1 | 2/2004 | Dahlinger | |
| 6,699,185 | B2 * | 3/2004 | Gminder et al. | 600/157 |
| 6,712,757 | B2 * | 3/2004 | Becker et al. | 600/121 |
| 6,755,782 | B2 | 6/2004 | Ogawa | |
| 6,767,322 | B1 | 7/2004 | Futatsugi et al. | |
| 7,341,556 | B2 * | 3/2008 | Shalman | 600/157 |
| 7,811,228 | B2 * | 10/2010 | Adams | 600/121 |
| 8,047,215 | B1 * | 11/2011 | Sasaki | 134/95.2 |
| 8,062,213 | B2 * | 11/2011 | Jerjomin | A61B 1/121 600/127 |
| 8,439,829 | B2 * | 5/2013 | Miyamoto | A61B 1/00091 600/121 |
| 2005/0234297 | A1 | 10/2005 | Devierre et al. | |
| 2006/0020165 | A1 * | 1/2006 | Adams | A61B 1/00094 600/121 |
| 2006/0173244 | A1 * | 8/2006 | Boulais et al. | 600/156 |
| 2007/0225556 | A1 | 9/2007 | Ortiz et al. | |
| 2008/0188715 | A1 * | 8/2008 | Fujimoto | 600/157 |
| 2008/0277853 | A1 | 11/2008 | Menn | |
| 2008/0319266 | A1 | 12/2008 | Poll et al. | |
| 2009/0247830 | A1 * | 10/2009 | Miyamoto | A61B 1/12 600/157 |
| 2009/0247831 | A1 * | 10/2009 | Miyamoto et al. | 600/157 |
| 2009/0253964 | A1 * | 10/2009 | Miyamoto | 600/157 |
| 2009/0253965 | A1 | 10/2009 | Miyamoto | |

FOREIGN PATENT DOCUMENTS

| | | |
|---|---|---|
| DE | 10024728 | 11/2001 |
| DE | 3004089 | 3/2011 |
| EP | 0497347 | 8/1992 |
| EP | 1046371 | 10/2000 |
| EP | 1721567 | 11/2006 |
| EP | 1607037 | 12/2006 |
| EP | 1462060 | 2/2007 |
| EP | 1803388 | 7/2007 |
| EP | 2106739 | 10/2009 |
| EP | 1259858 | 3/2011 |
| JP | 53108459 | 9/1978 |
| JP | 62143013 | 6/1987 |
| JP | 1204637 | 8/1989 |
| JP | 6098854 | 4/1994 |
| JP | 6237889 | 8/1994 |
| JP | 7095953 | 4/1995 |
| JP | 7246187 | 9/1995 |
| JP | 9138358 | 5/1997 |
| JP | 2001258824 | 9/2001 |
| JP | 2000083890 | 10/2001 |
| JP | 2002238906 | 8/2002 |
| JP | 2002301026 | 10/2002 |
| JP | 2003204928 | 7/2003 |
| JP | 2003210388 | 7/2003 |
| JP | 2004267255 | 9/2004 |
| JP | 200388490 | 10/2004 |
| JP | 2007244796 | 9/2007 |
| JP | 2007252559 | 10/2007 |
| WO | 8705795 | 10/1987 |
| WO | 9210969 | 7/1992 |
| WO | 0189371 | 11/2001 |
| WO | 2004016299 | 2/2004 |
| WO | 2006129472 | 7/2006 |
| WO | 2008062594 | 5/2008 |
| WO | 2008153841 | 12/2008 |

OTHER PUBLICATIONS

US 5,772,579, 06/1998, Reisdorf et al. (withdrawn).

* cited by examiner

FLOW GUIDE

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

CROSS-REFERENCE TO RELATED APPLICATION

This application claims priority to Application No. 0917857.5 filed on Oct. 12, 2009 in Great Britain.

FIELD OF THE INVENTION

The present invention relates to a flow guide for directing a fluid flow across a surface of a device in a controlled manner. Particularly, but not exclusively, the device is an endoscope and the surface comprises a surface of a lens or other optical surface.

The present invention will be discussed in relation to the optics of an endoscope and, in particular, with reference to that of a laparoscope, but by no means is it exclusive to these devices. It can also encompass commercial or other medical optic instrumentation as well as other devices.

BACKGROUND OF THE INVENTION

Endoscopes are used in minimally invasive surgery (MIS) by surgeons to permit remote visualisation and navigation within a body cavity inside a patient. They act as the eyes of the surgeon whilst a surgical procedure, tissue manipulation or diagnostic investigation is undertaken. One type of endoscope is a laparoscope for abdominal MIS, which is used in speciality areas such as laparoscopic general surgery including upper and lower gastrointestinal surgery, gynaecology, obesity surgery (bariatric surgery) and Urology, as well as other surgical sectors utilising a rigid scope or semi rigid scope, including thoracic and pulmonary, ENT, and neurological surgery.

Minimally invasive surgery (MIS), often referred to as "keyhole surgery" as well as Minimum Access Surgery (MAS) is defined as a surgical method using small abdominal skin incisions (or no abdominal skin incisions, in which case a natural orifice is used in conjunction with an internal incision) compared with classic open surgical procedures that require large incisions. In MIS, a special access port called a cannula is inserted into the skin incision through which a miniature camera is introduced into the body and transmits images to a video monitor, thereby allowing the physician to visualise, diagnose and, if necessary, treat a variety of conditions.

MIS is already an integrated part of daily surgical activity in surgical centres around the world. Many procedures are now performed by this "keyhole" approach using an appropriate endoscope, or by reduced open surgery (such as mini-open or laparoscopically assisted procedures or hand assisted laparoscopic surgery or single incision laparoscopic surgery), where the skin incision is reduced compared with only a few years ago. The development of these MIS approaches is rapidly on-going and development of new techniques that will aid patients and society because of reduced complications, patient morbidity and hospital stay compared with the corresponding "old" methods will continue to drive the majority of procedures to MIS.

The endoscope used in laparoscopy is called a laparoscope and is comprised of an elongated, typically cylindrical, shaft containing optical elements such as a camera, lighting provisions such as an optical fibre bundle and other equipment. During laparoscopy procedures, laparoscopes are used to visualise the target anatomy. In laparoscopy, the laparoscope is inserted through a cannula or port, which has been introduced through a small incision, next to the umbilicus (belly button) in the patient to access the abdominal cavity. The abdominal cavity is generally insufflated via this port (although other ports can be used) with medical grade carbon dioxide, or another suitable gas, via an insufflator device in order to expand or distend the abdominal cavity by elevating the abdominal wall and hence creating an operating space or environment. Insufflators for general surgical use within theatres are programmed to activate on and off to maintain and optimise the set pressure within the patient's abdominal cavity.

During a laparoscopic procedure, there are four main requirements for a surgeon or practitioner: continuous operative vision, maintained operative control, safety and time efficiency. The laparoscope or endoscope lens in an MIS procedure is the surgeon's "eyes" and the optics regularly become soiled by peritoneum or other bodily fluid, blood, aerosol fat, tissue particulate, smoke, debris or condensation, all of which impair the surgeon's vision (via an external monitor/screen). These various soiling components are disturbed by various instruments introduced into the abdominal cavity via working ports, such as electro-cautery coagulation devices, laparoscopic scissors, ultrasonic coagulation cutting devices, suction-irrigation devices and many others. Since these instruments are a crucial part of MIS and laparoscopic procedures, in general, they will remain as the main source of lens contamination. As a result of this contamination, visualisation via the laparoscope optics is regularly diminished and impaired.

Currently, the "gold standard" for soil removal and lens cleaning requires the laparoscope to be removed from the patient's abdominal cavity. The offending contamination is removed with a sterile swab, then the laparoscope optics are washed in hot sterile saline, then excess saline is removed with another clean swab and finally the lens is coated with a sterile anionic-surfactant (such as Fog Reduction Elimination Device (F.R.E.D.) or ClearIt™ anti-fog solution). From the moment of diminished visualisation, the scope is removed and an immediate stop in the surgical procedure occurs. During this period, the patient can be exposed to increased risk since the surgeon can no longer see the operating field. In other words, the surgeon is blinded. Further to this, there is an interruption in surgeon workflow and an increase in surgical theatre time and time of the patient being under general anaesthesia. Removal of the laparoscope for cleaning can occur up to 5-10 times per hour and the process of cleaning typically takes 40-60 seconds, thereby adding 3-10 minutes per hour of operative time and patient time under general anaesthesia. However, more importantly, the surgeon's workflow and concentration is broken, compromising patient safety. The safety issues associated with removing the laparoscope for cleaning are well understood and attempts have been made to solve this problem in the past. These attempts have been inadequate at solving the myriad of problems associated with cleaning the lens in-situ.

SUMMARY OF THE INVENTION

In one aspect of the invention, there is provided a flow guide for directing a fluid flow across a surface of a device, the flow guide including a locating arrangement for locating the device with respect to the flow guide such that the surface is disposed generally in a first plane defined along first and second mutually perpendicular directions, and a channel for guiding the fluid flow, the channel having sides spaced with respect to each other in the first direction, the flow guide also including a respective limb extending from each of the sides generally in the second direction, each limb defining a limb guide surface extending generally in a third direction perpendicular to the first and second directions and being convex in a plane parallel to the first plane to cause fluid flow from the channel to diverge in the first direction as it flows across the surface of the device.

In another aspect of the invention, there is provided a flow guide for guiding a fluid flow longitudinally along a device and directing the fluid flow across a transverse end surface of the device, the flow guide including: an inner surface that defines a space for receiving the device, a locating arrangement for locating the device with respect to the flow guide such that the transverse end surface of the device is disposed generally in a transverse plane fixed relative to the flow guide, and a channel for guiding the fluid flow longitudinally along the device and directing the fluid flow across the transverse end surface of the device, the channel having an inner and outer channel surface facing each other, the inner channel surface being closer to the space, wherein the inner channel surface extends through the transverse plane and an end portion of the inner channel surface meets the inner surface at an edge located substantially in the transverse plane and is disposed at a first acute angle to the transverse plane, and wherein the outer channel surface extends through the transverse plane and an end portion of the outer channel surface is disposed at a second acute angle to the transverse plane to direct the fluid flow towards the transverse plane.

In another aspect of the invention, there is provided a flow guide for guiding a fluid flow longitudinally along a device and directing the fluid flow across a transverse end surface of the device, the flow guide comprising a first portion and a second portion manufactured as a separate part from the first portion, wherein the first portion and the second portion cooperatively define: an inner surface that defines a space for receiving the device, a locating arrangement for locating the device with respect to the flow guide such that the transverse end surface of the device is disposed generally in a transverse plane, and a channel for guiding the fluid flow longitudinally along the device and directing the fluid flow across the transverse end surface of the device, the channel having an inner and outer channel surface facing each other, the inner channel surface being closer to the space, wherein an end portion of the inner channel surface meets the inner surface at an edge, the edge being located substantially in the transverse plane, wherein the outer channel surface extends through the transverse plane and an end portion of the outer channel surface is arranged to direct the fluid flow towards or substantially parallel to the transverse plane, wherein the second portion can be an insert for insertion into the first portion.

In some embodiments, one or more of the above aspects are combined.

In some embodiments, the flow guide is for guiding and directing the fluid flow to clear an end surface of the device. In some embodiments, the device is an endoscope and the end surface comprises the surface of the optics (such as a lens surface). The flow guide allows the surface of the lens to be cleaned of any biological or foreign material that becomes attached to the lens during surgery. The lens can therefore be cleaned without the endoscope having to be removed from the patient and this ensures that the surgeon can visualise the surgical site at all times.

In some embodiments, the flow guide comprises limbs, each of which has a convex limb guide surface that causes the fluid flow to diverge across the end surface in a controlled manner. This allows a relatively high-speed fluid flow, which is a generally parallel flow as it exits a channel in the flow guide, to diverge rapidly so that the flow covers a larger proportion of the end surface than it would be able to cover if the limbs were not present.

In some embodiments, an outlet defined by the flow guide and the end surface at the exit of the channel is narrower at its centre than at its edges. This causes the fluid flow to be at a higher speed through the centre of the outlet than at its edges and in doing so creates a fluid flow gradient. The slower fluid flow near the edges travels slowly enough to be able to attach to the limb guide surfaces, which cause the flow to diverge. The fluid flow near the centre of the outlet does not need to attach to a limb guide surface, and therefore is allowed to travel faster. Moreover, the non-uniform speed profile itself facilitates flow divergence even in embodiments where there are no limbs as described above.

In some embodiments, the flow guide is arranged to longitudinally guide the flow along the device and direct the flow across a transverse end surface of the device such that the fluid flow attaches to the end surface after leaving the outlet. This ensures that a large proportion of the fluid flow will act to dislodge any unwanted particles on the end surface, rather than not attaching and flowing away from the end surface, which would be of little or no use in cleaning the surface. Surface attachment is aided, for example, by a specifically shaped corner feature defined by an inner channel surface of the flow guide adjacent the end surface, which facilitates the prevention of flow separation.

In some embodiments, the flow guide is a single, retrofit, attachment for use on a standard device, such as a laparoscope. The attachment is of a simple construction and is therefore inexpensive to produce. This makes it suitable for being used as a disposable attachment. A non-disposable attachment would have to be thoroughly cleaned, freed from particulate contamination and re-sterilised between each surgical procedure.

In some embodiments, the flow guide is manufactured as two separate parts, with each part defining some of the geometric features of the flow guide. For example, the flow guide may have a separately manufactured (e.g. moulded) main portion and an insert for insertion into the main portion, thereby simplifying the manufacture of each part and allowing better manufacturing tolerances to be achieved.

In some embodiments, the flow guide is configured such that a portion of the device or endoscope extends longitudinally clear beyond a lowered portion of the flow guide transversely opposite the outlet. This enables the flow across the end surface to clear the end surface more efficiently at its edges, thereby facilitating cleaning of the end surface. In other words, in these embodiments, there is a gap between the lowered portion and the plane in which the end surface is disposed in use. For example, the lowered portion may extend on each side of the outlet or any other guide arrangements adjacent the outlet, such as the limbs described above. The lowered portion may extend over the entire remaining perimeter of the flow guide, whether the flow guide completely encloses the device or encloses it only partially.

In some embodiments, the flow guide is arranged to fully enclose the device along a perimeter while in others it is arranged to only partially enclose it, for example with wings extending on either side of the outlet. In both cases, these embodiments are arranged to hold the device securely, preventing relative movement transversely but allowing the device to be slidably inserted into the flow guide.

In some embodiments, the flow guide is integrally formed with a laparoscope (or, generally, an endoscope). This ensures that the flow guide is permanently in position and can be used at any time when the device is being used.

In some embodiments, the flow guide has an inner surface that defines a space for receiving the device when the device is slid longitudinally into the space. In some embodiments, the inner surface encloses more than half of a transverse perimeter of the device, which acts to secure the device with respect to the flow guide. In some embodiments, when the device is inserted into the flow guide, the transverse end surface of the device protrudes longitudinally beyond parts of the inner surface.

In some embodiments, the flow guide comprises a first portion and a second portion manufactured as a separate part from the first portion, for example, as an insert for insertion into the first portion, the first portion and the second portion cooperatively defining the channel. In some embodiments, the first portion and the second portion have been moulded with separate moulds. In some embodiments, the inner channel surface, the edge and at least a portion of the inner surface are defined by the insert. In some embodiments, the outer channel surface is defined by the first portion.

In some embodiments, an edge of the outer channel surface is convex in a plane perpendicular to the transverse plane to define an outlet of non-uniform height relative to the transverse plane, thereby imparting a non-uniform velocity profile to fluid constrained to flow between the edge of the outer channel surface and the transverse plane.

In some embodiments, the locating arrangement includes a base of a limb disposed generally in the transverse plane for stopping the transverse end surface of the device, thereby defining the transverse plane. In some embodiments, the flow guide includes a respective limb extending transversely from each side of the edge, each limb defining a limb guide surface extending generally longitudinally and being convex in a plane parallel to the transverse plane to cause fluid flow from the channel to diverge in the plane parallel to the transverse plane as it flows across the transverse end surface of the device.

In some embodiments, the locating arrangement includes a base of the limb disposed generally in the first plane and arranged to rest against the surface of the device so that the limb guide surfaces extend in the third direction from the surface of the device.

In some embodiments, the inner channel surface has a crest above the transverse plane, and a projection of the crest onto the transverse plane is closer to a line defined by the intersection of the inner channel surface and the transverse plane than it is to the edge. In some embodiments, a longitudinal portion of the inner channel surface extends only partially along the space.

In some embodiments, the end portion of the inner channel surface is arranged to form a substantially continuous surface with the transverse end surface of the device.

In some embodiments, the inner channel surface extends through the transverse plane and the end portion of the inner channel surface meets the inner surface at the edge and is disposed at a first acute angle to the transverse plane, and the end portion of the outer channel surface is disposed at a second acute angle to the transverse plane to direct the fluid flow towards the transverse plane.

In some embodiments, the second acute angle is different from the first acute angle, for example, with the second acute angle being larger than the first acute angle. In some embodiments, the mean of the first and second acute angles is approximately 20°. In some embodiments, the first acute angle is approximately 15° and the second acute angle is approximately 26°.

In some embodiments, the channel comprises a chamber between a portion of the channel adjacent the edge and a longitudinal portion of the channel extending longitudinally along the space, the chamber being shaped to turn the fluid flow from flowing longitudinally along the longitudinal portion of the channel to flowing generally transversely through the portion of the channel adjacent the edge. In some embodiments, the chamber is shaped to turn the flow through an angle of approximately 110°. In other embodiments, the chamber is shaped to turn the flow through an angle of approximately 124°. In some embodiments, the chamber has a larger cross-sectional flow area than the portion of the channel adjacent the edge. In some embodiments, the chamber has a larger cross-sectional flow area than the longitudinal portion of the channel adjacent the chamber.

In some embodiments, the flow guide has an inlet at an end of the flow guide longitudinally spaced from the edge, wherein the inlet has a larger cross-sectional flow area than the channel adjacent the edge. In some embodiments, the cross-sectional flow area of the inlet is larger than the cross-sectional flow area of an outlet defined between an end of the outer channel surface and the transverse plane. In some embodiments, the cross-sectional flow area of the inlet is larger than the cross-sectional flow area of the outlet by a factor of approximately six. In some embodiments, the factor is approximately 15. In some embodiments, the factor is at least 6, at least 10, or at least 15. In some embodiments, the channel is continuous and has no internal obstructions to fluid flow.

In some embodiments, the cross-sectional flow area of the channel decreases from the inlet to an entrance of the chamber.

In some embodiments, the cross-sectional flow area of the chamber increases after the entrance.

In some embodiments, the end portions of the inner and outer channel surfaces are for directing the fluid flow so that, when the transverse end surface of the device is disposed generally in the transverse plane, the fluid flow attaches to the transverse end surface of the device and flows across it.

In some embodiments, the inner channel surface, the edge and at least a portion of the inner surface are defined by the second portion. In some embodiments, the locating arrangement is defined by the first portion. In some embodiments, the second portion extends only partially along the space.

In some embodiments, the edge of the outer channel surface is symmetrical about a third plane perpendicular to the first and second planes. In some embodiments, the edge of the outer channel surface is curved.

In some embodiments, each of the limb guide surfaces is generally curved in a plane defined by the first and second directions.

In some embodiments, the edge of the outer channel surface is convex in a plane defined by the first and second directions.

In some embodiments, the flow guide is arranged to direct the fluid flow at an angle of approximately 20° to the first plane.

In some embodiments, the channel has an inner channel surface extending in the first direction between the sides of the channel, the inner channel surface generally facing the outer channel surface. In some embodiments, the inner channel surface is shaped to form a substantially continuous surface with the surface of the device when the device is secured to the flow guide. In some embodiments, an inner channel surface facing the outer channel surface is defined by the device when the device is located such that the surface is disposed in the first plane.

In some embodiments, the device is substantially cylindrical and the surface is an end surface of the device, wherein the flow guide is arranged to define a portion of the channel longitudinally along the device for guiding the fluid flow longitudinally along the device.

In some embodiments, a longitudinal portion of the flow guide comprises an inner surface and an outer surface, the inner surface and outer surface being connected to form two tips so that the device is only partially enclosed by the longitudinal portion. In some embodiments, a distal tip surface is defined between the inner surface and the outer surface adjacent each tip, the distal tip surfaces being in a plane parallel to the first plane but not coplanar with the first plane, such that the surface of the device protrudes longitudinally beyond the distal tip surfaces when the surface of the device is disposed in the first plane.

In another aspect of the invention, there is provided an optical device comprising a transverse end surface including a lens or optical window and a flow guide as described above for guiding a fluid flow longitudinally along the device and directing the fluid flow across the transverse end surface of the device, wherein the flow guide is integrally formed with the device or detachable from the device.

In some embodiments, the device is substantially cylindrical and the surface is an end surface of the device. In some embodiments, the device is an optical device and the surface includes a lens or optical window of the device. In some embodiments, the device is a medical device, or an endoscope, or a laparoscope.

BRIEF DESCRIPTION OF THE DRAWINGS

Embodiments of the invention are now described by way of example only and with reference to the accompanying drawings, in which.

DETAILED DESCRIPTION OF PREFERRED EMBODIMENT

Figure 1:
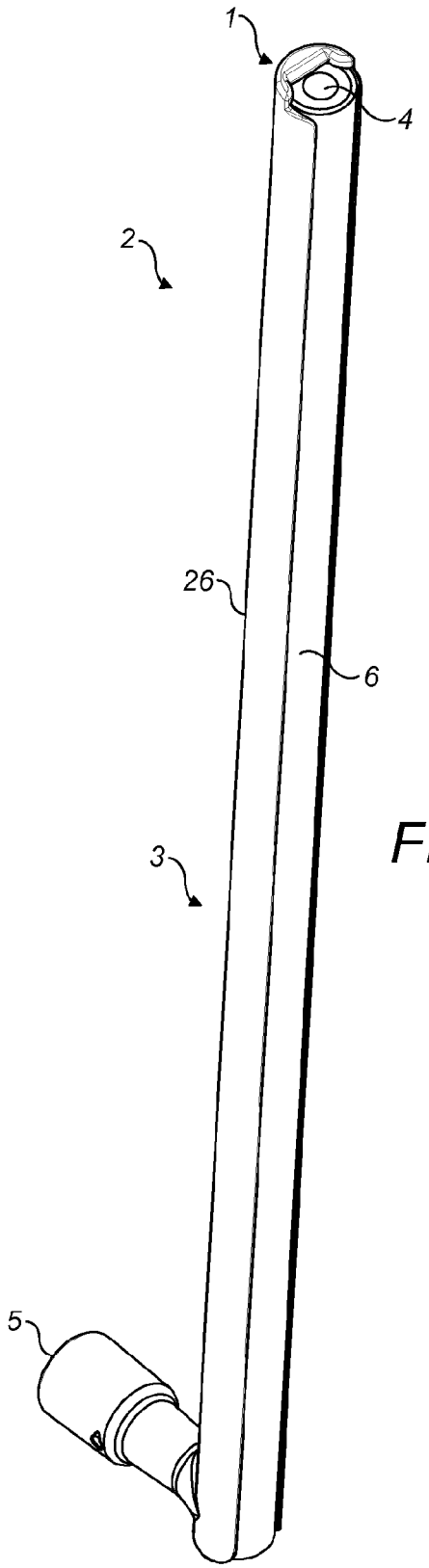
FIG. 1 depicts a view from a raised perspective of a flow guide attached to the full length of a laparoscope (endoscope), with an end surface (optics) of the laparoscope in view.

With reference to FIG. 1, a flow guide 2 is attached to a laparoscope 6, which is generally cylindrical or rod-shaped. The flow guide 2 is for guiding a fluid flow longitudinally along the laparoscope 6 and directing the fluid flow across a substantially flat distal end surface 4 of the laparoscope 6. The flow guide 2 is arranged to promote laminar flow of the fluid across the end surface 4 of the laparoscope 6. The flow guide 2 comprises a longitudinal portion 3 for guiding the fluid flow in a longitudinal direction along the shaft of the laparoscope 6, a distal end portion 1 for directing the fluid flow across the end surface 4 to clean the end surface 4 and an inlet 5 at an opposite end. The end surface 4 (shown in more detail in FIG. 2) is disposed generally in a transverse plane. (i.e. a plane, perpendicular to the longitudinal direction, that is fixed relative to the flow guide 2) and comprises a lens 4a, optical window, or other surface of the laparoscope 6, surrounded by a fibre optic bundle 4b, which acts as a light source.

The flow guide 2 includes a channel 8 (visible in FIG. 6) through which fluid is able to flow. The channel 8 has an outlet 10 through which the fluid exits the channel 8 at the distal end portion 1 of the flow guide 2. In use, the flow guide 2 is located in a fixed position relative to the laparoscope 6. The flow guide 2 is attachable to the laparoscope 6 such that the fluid flow leaving the channel 8 through the outlet 10 is directed across the end surface 4 of the laparoscope 6.

The channel 8 comprises two sides 12 (visible in FIG. 5), which are spaced with respect to each other in a first direction parallel to the end surface 4. The two sides 12 face towards each other on opposite sides of the channel 8 and are connected by an outer channel surface 14 (visible in FIG. 6), which defines the outer surface of the channel 8 (i.e. the surface furthest from the laparoscope 6). At the distal end portion 1, the outer channel surface 14 faces generally towards the end surface 4, and defines an outer edge 16 that extends substantially in the first direction between the two sides 12 and defines an outer limit of the outlet 10. An inner limit of the outlet 10 is defined, in some embodiments, by an inner channel surface 35 (described in detail below). In some embodiments, the inner limit of the outlet 10 is defined cooperatively by the inner channel surface 35 and by the end surface 4 itself, while in other embodiments, only one of these defines the inner limit of the outlet 10. Proximal to the outer edge 16, the outer channel surface 14 is substantially straight in a direction parallel to the intended direction of fluid flow. This helps to prevent the fluid flow from converging to a single point after it passes through the outlet 10.

At the opposite end of the flow guide 2 to the distal end portion 1 of the flow guide 2, the inlet 5 is formed in the flow guide 2. The inlet 5 allows fluid to flow into the portion of the channel 8 in the longitudinal portion 3 of the flow guide 2, to flow along the laparoscope 6 to a chamber 42 (described below), then to the portion of the channel 8 in the distal end portion 1 of the flow guide 2 and out through the outlet 10. In the portion of the channel 8 along the laparoscope 6, the fluid re-establishes laminar flow after it has passed through the inlet 5 as it travels along the laparoscope 6.

The cross-sectional flow area of the inlet 5 is larger than that of the outlet 10. (Throughout this description, the term 'cross-sectional flow area' refers to the cross-sectional area in a plane perpendicular to the intended direction of fluid flow.) These two cross-sectional flow areas differ by a factor of six, though in some embodiments the factor is different. The inlet 5 has a cross-sectional flow area of approximately 14.2 $mm^2$ and the outlet 10 has a cross-sectional flow area of approximately 2.4 $mm^2$. This difference in cross-sectional flow area causes the fluid flow to leave the outlet 10 at a generally higher speed than the speed at which it enters the inlet 5. This increased exit speed helps the fluid flow to have sufficient speed to attach to and dislodge any unwanted particles on the end surface 4 of the laparoscope 6.

In some embodiments, the inlet 5 at the opposite end of the flow guide 2 to the distal end portion 1 is positioned at an angle of approximately 15° with respect to the normal to the longitudinal axis of the laparoscope 6. The incoming fluid turns through an angle of approximately 75° as it flows from the inlet 5 into the channel 8 and towards the distal end of the channel 8. In some embodiments, the cross-sectional flow area of the inlet 5 is approximately 25 $mm^2$, more specifically 25.32 $mm^2$. The cross-sectional flow area of the inlet 5 is larger than that of the outlet 10. These two cross-sectional flow areas differ by a factor of approximately 15.

The inlet 5 is connected to a fluid supply (not shown). In some embodiments, the fluid that is received from the fluid supply is a gas, such as carbon dioxide. The gas flow that is manipulated and controlled by the flow guide 2 is used to clean the end surface 4 by dislodging any unwanted particles from it. The unwanted particles include biological or foreign material that becomes attached to the surface of the lens during surgery.

In some embodiments, the fluid that is received from the fluid supply is a liquid, and a jet of liquid is expelled through the outlet 10 across the end surface 4. In some embodiments, this jet of liquid is used to clean the end surface 4 in a similar manner as described above.

Figure 2:
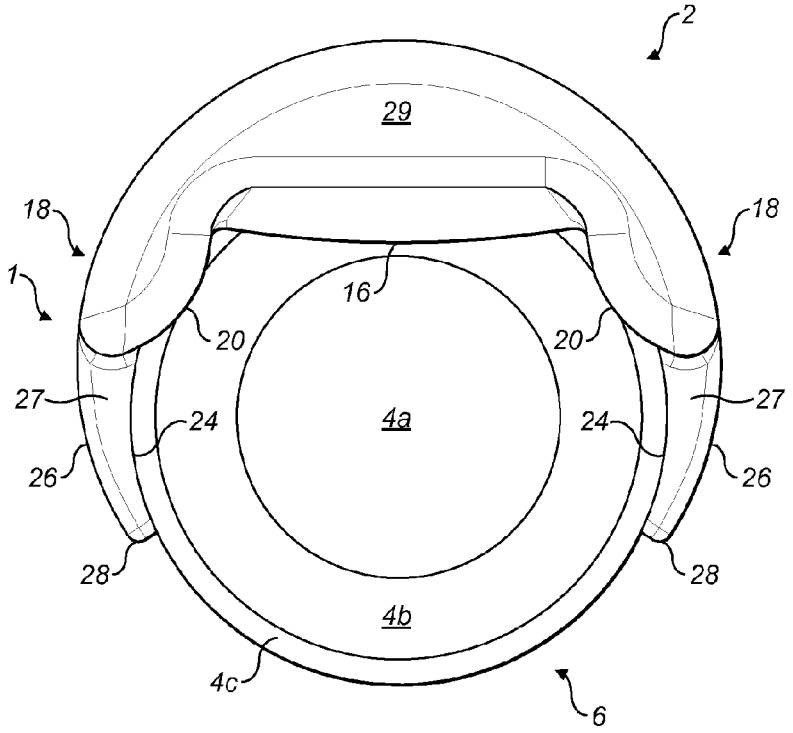
FIG. 2 depicts a face-on or top view of a distal end surface of the laparoscope with the flow guide attached to it.

Referring to FIG. 2, which provides a more detailed view of the end surface 4 of the laparoscope 6, there are three main parts of the end surface 4 of the laparoscope 6. The lens 4a or optical window is in the centre. The lens 4a is surrounded by the fibre optic bundle 4b, which is used to direct light away from the end surface 4 so that the laparoscope 6 can be used in an otherwise unlit environment. The fibre optic bundle 4b is surrounded by an outer cover 4c, which extends longitudinally along the outside of the laparoscope 6 and protects the inner parts of the laparoscope 6. Part of an outer surface of the outer cover 4c is in contact with an inner surface 24 of the flow guide 2. The details of the end surface 4 of the laparoscope 6 are omitted from subsequent Figures for the sake of clarity of presentation.

In some embodiments, the outer edge 16 of the outer channel surface 14 partially extends up to or partially over the lens 4a of the laparoscope 6 in the longitudinal direction. The proximity of the outlet 10 to the lens 4a ensures that fluid directed to flow over the lens 4a does so at a high speed and does not lose a significant amount of speed before reaching the lens 4a, as would happen if the outlet 10 were far from the lens 4a.

The longitudinal portion 3 of the flow guide 2 extends from the distal end portion 1 of the flow guide 2 along the shaft of the laparoscope 6 to its proximal end in a direction that is generally perpendicular to the end surface 4 of the laparoscope 6. The longitudinal portion 3 of the flow guide 2 comprises the inner surface 24 and an outer surface 26. The inner surface 24 defines a space for receiving the laparoscope 6, and is shaped to enclose at least part of the laparoscope 6 to attach the flow guide 2 to the laparoscope 6. In some embodiments, when the flow guide 2 is attached to the laparoscope 6, the outer surface 26 substantially defines an arc of a circle in a plane parallel to the transverse plane. The outer surface 26 and inner surface 24 extend longitudinally along the axis of the laparoscope 6. The inner surface 24 and outer surface 26 are connected to form two tips 28, with one tip 28 at each end of the arc defined by the outer surface 26 so that the laparoscope is only partially enclosed by the longitudinal portion 3. The inner surface 24 wraps around more than half of the circumference of the laparoscope 6 to prevent the laparoscope 6 moving in a transverse direction relative to the flow guide 2.

Figure 3:
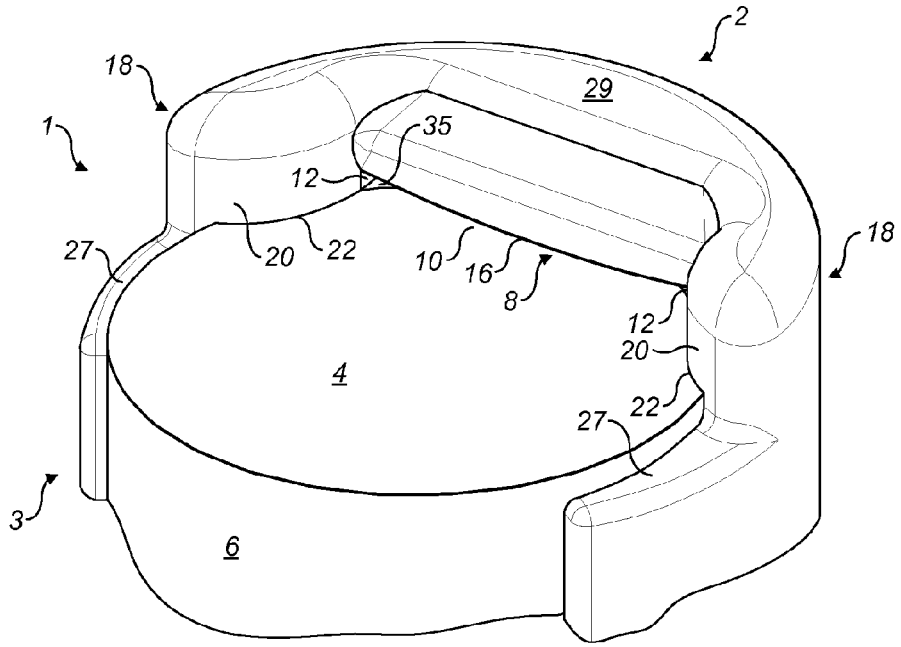
FIG. 3 depicts a view from a raised perspective of a distal end portion of embodiments of the flow guide attached to the laparoscope.

With reference to FIG. 3, adjacent each tip 28, a distal tip surface 27 is defined between the inner surface 24 and the outer surface 26. The distal tip surfaces 27 are in a plane parallel to the transverse plane but are not coplanar with the transverse plane. Rather, they are a relatively small distance away from the transverse plane in the longitudinal portion 3 of the flow guide 2. In some embodiments, this distance is about 0.5 mm. When the laparoscope 6 is inserted into the flow guide 2, the end surface 4 of the laparoscope 6 protrudes longitudinally beyond the distal tip surfaces 27. Situating the distal tip surfaces 27 in this way means that the edge of the end surface 4 is clear from any obstructions so that particles on the end surface 4 can be moved off the end surface 4 by the fluid flow. Other than the parts that meet the distal tip surfaces 27, the remainder of the outer surface 26 extends longitudinally through the transverse plane.

In some embodiments, the tips 28 are substantially rigid and in order to position the laparoscope within the flow guide 2, the laparoscope 6 is slid longitudinally into the space for receiving the laparoscope 6. In other embodiments, the tips 28 are flexible and can be separated so that the laparoscope 6 can be inserted between them so that they exert a force on the laparoscope 6 to secure the laparoscope 6 relative to the flow guide 2. In other embodiments, the tips 28 are flexible and they exert a force on the laparoscope 6 to secure the laparoscope 6 relative to the flow guide 2, but the laparoscope 6 is inserted by being slid longitudinally into the space for receiving the laparoscope 6.

In some embodiments, the flow guide 2 holds the laparoscope 6 in place due to an elastic force on the laparoscope 6 when it is in the flow guide 2. The tips 28 are bent inwards such that they grip the laparoscope 6 when it is in the flow guide 2. In other embodiments, the elastic force is applied without the tips 28 being bent inwards.

The flow guide 2 also comprises two limbs 18. Each limb 18 extends from a respective one of the sides 12 of the channel 8 generally in a second direction, which is perpendicular to the first direction. The second direction is generally parallel to the direction of the fluid flow across the end surface 4 as it passes through the outlet 10. Each limb 18 comprises a limb guide surface 20, which extends generally in a third direction that is perpendicular to the end surface 4 and is perpendicular to the first and second directions. At the outlet 10, there is a smooth transition between each side 12 of the channel 8 and the respective limb guide surface 20. The limb guide surface 20 extends further in the third direction than the outlet 10, which is limited in its extent in the third direction by the outer channel surface 14. Each limb guide surface 20 also extends generally in the second direction away from the outlet 10. As each limb guide surface 20 extends in the second direction away from the outlet 10, it also extends in the first direction away from the opposing limb guide surface 20. The distance between the limb guide surfaces 20 along an imaginary line extending in the first direction therefore increases as the line moves in the second direction away from the outlet 10. The limb guide surfaces 20 therefore diverge as they extend in the second direction. The angle of divergence of each limb guide surface 20 with respect to the second direction increases with distance from the outlet 10. In other words, the limb guide surface 20 is convex. In some embodiments, proximal to the outlet 10, the limb guide surface 20 extends substantially in the second direction, whereas, distal to the outlet 10, the limb guide surface 20 is generally along the first direction. In some embodiments, the limb guide surface 20 is smoothly curved in a plane defined by the first and second directions. In some embodiments, the limb guide surface 20 is formed by a plurality of substantially flat surfaces, which are arranged side by side to form a generally curved approximation of the smoothly curved surface. Both types of surfaces can collectively be described as generally curved.

Figure 5:
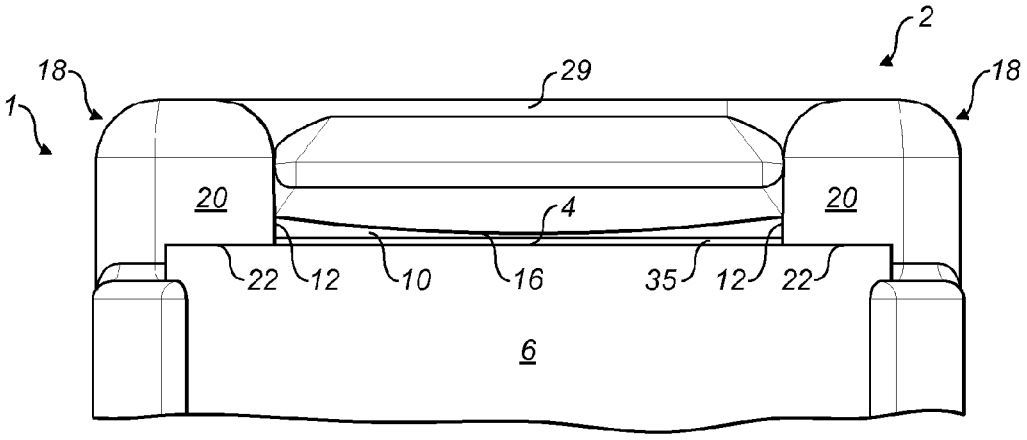
FIG. 5 depicts a side view of the distal end portion of the flow guide of these embodiments from the plane of the distal end surface of the laparoscope.

Each of the limbs 18 also comprises a base 22 (see FIG. 5). The bases 22 are shaped and disposed in the transverse plane so as to lie against a part of the end surface 4 of the laparoscope 6. Because the bases 22 rest against the end surface 4, this ensures that the limb guide surface 20 is in contact with the end surface 4 and extends in the third direction from the end surface 4. The location of the bases 22 also ensures that the outlet 10 is positioned correctly with respect to the end surface 4 so that the end surface 4 is disposed generally in the transverse plane. The bases 22 also act as stops, which hinder movement of the laparoscope 6 in the third (longitudinal) direction relative to the flow guide 2 beyond the transverse plane.

After curving away from the outlet 10, each of the limb guide surfaces 20 meets the outer surface 26. Each of the distal tip surfaces 27 extends from the respective tip 28 to a position coinciding in the longitudinal direction with the meeting point of the respective limb guide surface 20 and the outer surface 26.

In some embodiments, each limb guide surface 20 has a radius of curvature in a plane parallel to the end surface 4 of the laparoscope 6 of approximately 2.5 mm.

At the distal end portion 1 of the flow guide 2, a distal end surface 29 of the flow guide 2 extends from the outer edge 16 of the outer channel surface 14 away from the outlet 10 and meets with the outer surface 26 of the flow guide 2. Proximal to the outer edge 16 of the outer channel surface 14, the distal end surface 29 of the flow guide 2 extends generally in the third direction away from the outlet 10 (see FIG. 6). This helps to prevent the fluid flow from attaching to the distal end surface 29 as it passes through the outlet 10. As the distal end surface 29 extends away from the outlet, it also curves towards the outer surface 26 of the laparoscope 6. Proximal to the outer surface 26 of the flow guide 2, the distal end surface 29 of the flow guide 2 is substantially in a plane defined by the first and second directions, and is therefore perpendicular to the outer surface 26. As the limb guide surfaces 20 extend in the third direction away from the end surface 4 of the laparoscope 6, they meet with the distal end surface 29 of the flow guide 2. The distal end surface 29 of the flow guide 2 does not protrude in a plane defined by the first and second directions beyond the limb guide surfaces 20 or the outer edge 16 of the outer channel surface 14. This ensures that the distal end surface 29 of the flow guide 2 does not obstruct the uncovered parts of the end surface 4.

Figure 4:
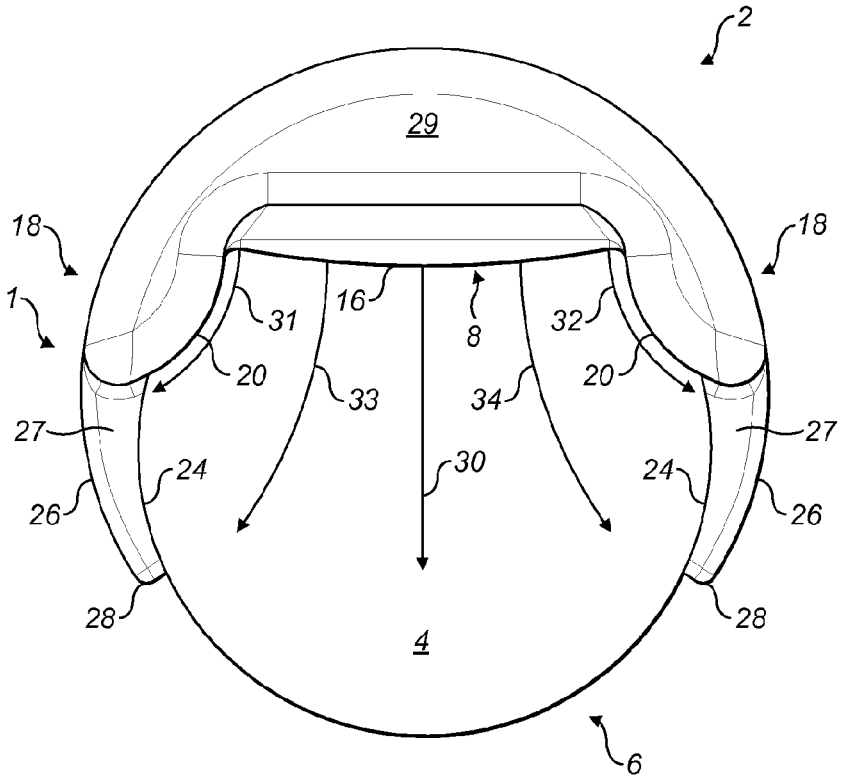
FIG. 4 depicts a face-on or top view of the distal end surface of the laparoscope with the flow guide of these embodiments attached to it.

With reference to FIG. 4, which shows the distal end portion 1 of the flow guide 2 and the end surface 4 of the laparoscope, the fluid flow path across the end surface 4 is shown by five arrows. A first arrow 30 shows the path of fluid across the centre of the end surface 4. This part of the fluid flow has a substantially linear path in the second direction. A second arrow 31 and a third arrow 32 illustrate the fluid flow adjacent each of the limb guide surfaces 20. The fluid flow adjacent the respective limb guide surface 20 has a tendency to attach to the limb guide surface 20 believed to be due to the Coandă effect. The fluid flow adjacent the limb guide surface 20 therefore has a velocity characterised by the respective limb guide surface 20 (i.e. the fluid flow follows a generally curved path). This causes the fluid flow adjacent the limb guide surfaces 20 to diverge in the first direction such that the fluid flow as a whole flows across substantially the entire end surface 4, other than the parts of the end surface 4 that are behind the limb guide surfaces 20, i.e. those that are in contact with the bases 22 of the limbs 18. A fourth arrow 33 and a fifth arrow 34 show the fluid flow at two intermediate positions between the centre of the outlet 10 and the limb guide surfaces 20. The flow paths in these positions are also affected by the limb guide surfaces 20 so that they also curve away from the arrow 30, but to a lesser extent than the flow paths shown by arrows 31 and 32.

The limb guide surfaces 20 help the flow to spread out sufficiently to cover substantially the entire exposed surface of the lens. Without the limb guide surfaces 20, the fluid flow would not be able to diverge as much or as quickly and therefore the fluid flow would be less able to protect and clear the lens adequately.

Referring again to FIG. 4, it can be seen that the outer edge 16 of the outer channel surface 14 is curved in a plane defined by the first and second directions and is convex in this plane. The centre of the outer edge 16 of the outer channel surface 14 extends further in the second direction than the parts of the outer edge 16 of the outer channel surface 14 that meet the sides 12 of the channel 8. The outer edge 16 is curved such that the fluid flow is perpendicular to the outer edge 16 as it flows through the outlet 10. This ensures that the fluid flow passes through the outlet 10 without being disrupted and it also helps the fluid flow to begin to diverge.

FIG. 5 shows a view of the distal end portion 1 of the flow guide 2 from a viewpoint in the plane of the end surface 4 of the laparoscope 6. It can be seen that the outlet 10 is defined by the two sides 12 of the channel 8, the outer edge 16 of the outer channel surface 14 and the end surface 4 of the laparoscope 6. The outer edge 16 of the outer channel surface 14 is curved in a plane defined by the first and third directions so that the gap between the outer edge 16 and the end surface 4 is smaller at the centre of the outer edge 16 than at the parts of the outer edge 16 adjacent the sides 12 of the channel 8. Adjacent the outer edge 16, the outer channel surface 14 itself is curved in the same way. The convex shape of the outer edge 16 ensures that fluid flows more quickly through the centre of the outlet 10 than through the parts of the outlet 10 adjacent one of the sides 12 of the channel 8. Fluid flowing above a certain speed through the outlet 10 adjacent a side 12 of the channel 8 would not attach to the limb guide surface 20 and would therefore continue in a path predominantly in the second direction and therefore not diverge across the end surface 4. The convex shape of the outer edge 16 in the plane defined by the first and third directions allows the average speed of flow to be increased while ensuring fluid attachment to the limb guide surfaces 20 due to the reduced flow speed in their vicinity relative to the flow speed at the centre. The velocity profile created by the outlet 10 aids flow attachment to the limb guide surfaces 20 but also causes flow divergence by itself. Fluid flow at the centre of the outlet 10 (along the first arrow 30 of FIG. 4) has a further distance to travel across the end surface 4, so the increased speed helps to keep the fluid flow attached to the end surface 4 across the entire end surface 4. The speed profile imparted by the convex shape of the outer edge 16 further helps divergence of the flow by itself (even in embodiments which do not have the limbs 18 defining limb guide surfaces 20) due to the friction between portions of the flow moving at different speeds.

In some embodiments, the outlet 10 is approximately 5.5 mm wide in the first direction. It is approximately 0.3 mm high in the third direction at the centre of the outlet 10 and approximately 0.7 mm high in the third direction adjacent each of the sides 12 of the channel 8. The outer edge 16 of the outer channel surface 14 forms an arc with a radius of approximately 9.5 mm.

In some embodiments, the cross-sectional flow area of the outlet 10 is approximately 1.7 $mm^2$, more specifically 1.68 $mm^2$. The outlet 10 is approximately 7 mm wide in the first direction. It is approximately 0.2 mm (more specifically 0.17 mm) high in the third direction at the centre of the outlet 10 and approximately 0.4 mm (more specifically 0.39 mm) high in the third direction adjacent each of the sides 12 of the channel 8. The outer edge 16 of the outer channel surface 14 forms an arc with a radius of approximately 28 mm, more specifically 27.51 mm.

At the distal end portion 1 of the flow guide 2, the channel 8 is arranged such that fluid flow is encouraged to attach to the end surface 4 as it leaves the channel 8 through the outlet 10. The attachment of the fluid flow to the end surface 4 ensures that the fluid flow is dedicated to removing unwanted particles from the surface of the lens. Any part of the fluid flow not attaching to the end surface 4 would flow away from the end surface 4 and be of little use in clearing the end surface 4.

Figure 6:
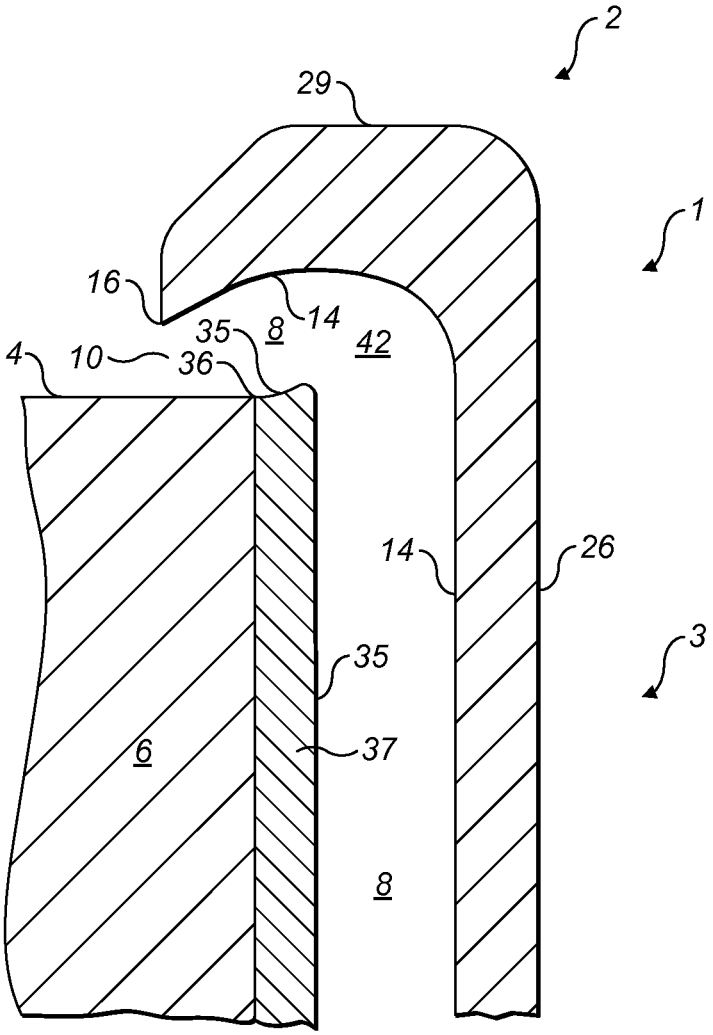
FIG. 6 depicts a cross-section of part of the distal end portion of the flow guide of these embodiments and part of the laparoscope when the flow guide is attached to the laparoscope.
Figure 7:
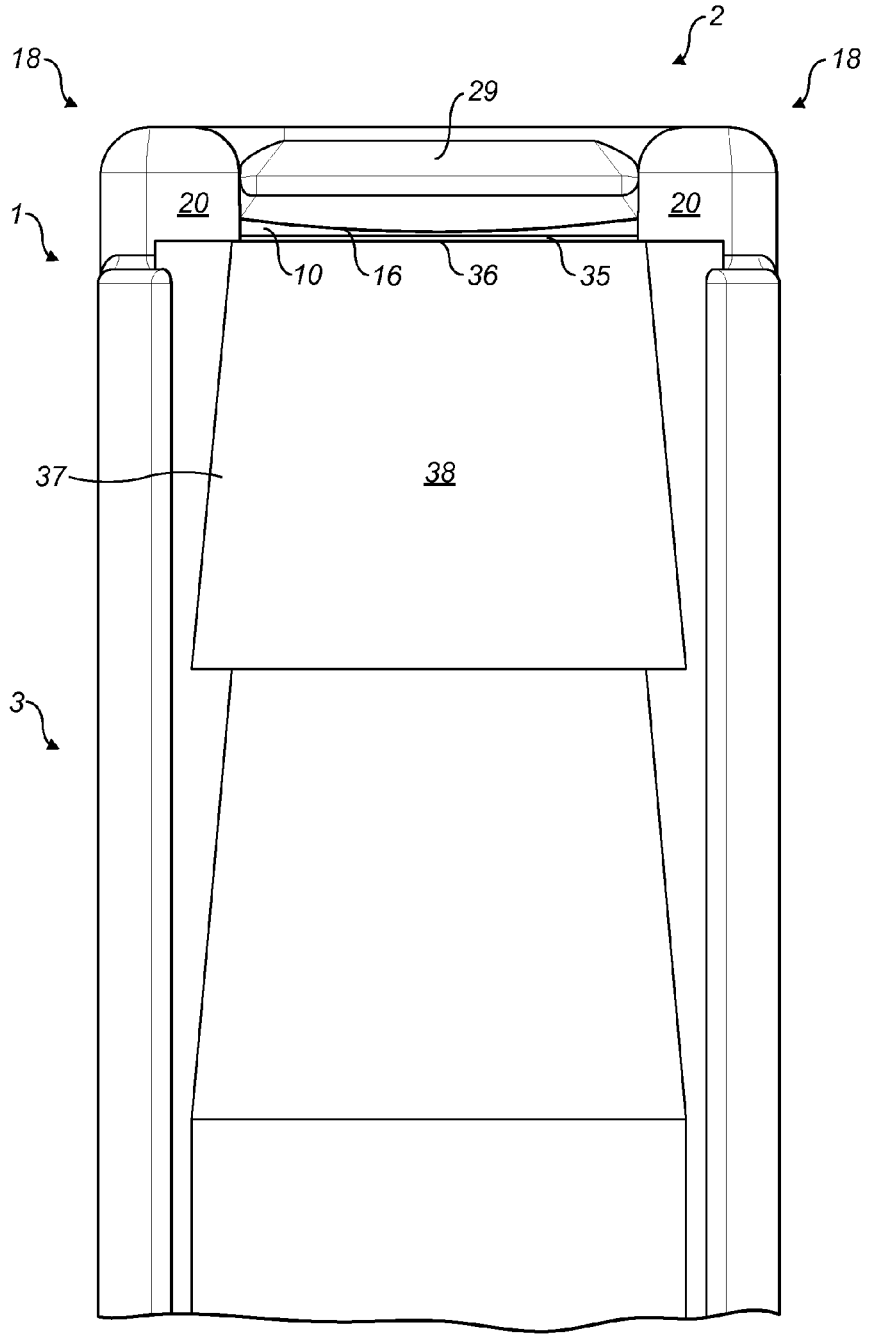
FIG. 7 depicts a side view of the distal end portion of the flow guide of these embodiments without the laparoscope, showing an insert positioned in the flow guide.

FIG. 6 depicts a longitudinal cross-section of part of the distal end portion 1 and part of the longitudinal portion 3 of the flow guide 2 and part of the laparoscope 6, and FIG. 7 depicts a side view of the distal end portion 1 and part of the longitudinal portion 3 of the flow guide 2. With reference to these Figures, in accordance with some embodiments, an insert 37 is located on an inner aspect of the flow guide 2. The insert 37 is manufactured separately from the remainder of the flow guide 2 (i.e. a main portion of the flow guide 2). In some embodiments, the insert 37 and main portion are separately moulded.

In some embodiments, the insert 37 defines the sides 12 of the channel 8 in the region of the longitudinal portion of the flow guide 2 in which the insert 37 is located. In other embodiments, the sides 12 of the channel in this region are defined by the main portion of the flow guide 2.

The insert 37 is arranged to be located at a location within the main portion of the flow guide 2 so that it extends between the sides 12 of the channel 8 and defines an inner channel surface 35, which is situated opposite and facing the outer channel surface 14 and extends from the distal end portion 1 partially along the longitudinal portion 3. The inner channel surface 35 is arranged to form a substantially continuous surface with the end surface 4 of the laparoscope 6. An inner edge 36 of the inner channel surface 35 adjacent the surface of the laparoscope 6 is therefore concave. The inner edge 36 is disposed substantially in the transverse plane. At the inner edge 36, the inner channel surface 35 meets an inner insert surface 38. The inner insert surface 38 is a surface of the insert 37 that is arranged to form a continuous surface with the inner surface 24 of the flow guide 2 when the insert is in its intended location. Thus, the inner insert surface 38 is in contact with the laparoscope 6 when the laparoscope 6 is located in its intended position within the flow guide 2, i.e. with its end surface 4 in the transverse plane.

In some embodiments, the portion of the inner channel surface 35 along the laparoscope 6 extends from the chamber 42 to the inlet 5. In other embodiments, the portion of the inner channel surface 35 along the laparoscope 6 extends from the chamber 42 to a position between the chamber 42 and the inlet 5, due to the insert 37 extending only as far as this position. In the remaining portion of the channel 8 along the laparoscope 6, the laparoscope 6 acts to define an equivalent of the inner channel surface 35.

In some embodiments, the insert 37 is separately moulded and then assembled with the remainder of the flow guide 2, for example by adhesive bonding, press-fitting, ultrasound or thermal-bonding. This allows the mould for the remainder of the guide to be simplified. In some embodiments, however, the "insert" 33 and the remainder of the flow guide 2 are moulded integrally as one piece in one single mould, that is, the flow guide 2 is moulded as a single unit.

In some embodiments, the insert 37 extends along substantially the entire longitudinal extent of the flow guide 2, such as from the inlet to the outlet.

Adjacent the inner edge 36, the inner channel surface 35 is disposed at a first angle to the end surface 4. Adjacent the outer edge 16, the outer channel surface 14 is disposed at a second angle to the end surface 4. The second angle is larger than the first angle. This causes the cross-sectional flow area of the channel 8 to reduce before it reaches the end surface 4 as the fluid flows towards the outlet 10, which increases the speed of the fluid flow prior to attachment to the end surface 4. In some embodiments, the mean of the first and second angles is approximately 20°. It has been found that fluid flow approaching the end surface 4 at this angle is more likely to attach to the end surface 4 and will stay attached to the end surface 4 for a longer duration. In some embodiments, the first angle is approximately 15°, more specifically, approximately 15.1° and the second angle is approximately 26°, more specifically, approximately 26.4°.

Both the inner channel surface 35 and the outer channel surface 14 extend through the transverse plane from the longitudinal portion 3 of the flow guide 2 to the distal end portion 1 of the flow guide 2. The channel 8 therefore extends through the transverse plane and then turns through an angle of more than 90°, about 110° in some embodiments, so that it is directed towards the transverse plane. The inner channel surface 35 extends in the third direction from the longitudinal portion 3 of the flow guide 2 to the distal end portion 1 and passes through the transverse plane. It curves smoothly through an angle of more than 90° (in some embodiments, approximately 105°, more specifically, approximately) 105.1°) until it is disposed in the first angle towards the transverse plane. The remainder of the inner channel surface 35 defines an end portion of the inner channel surface 35 and is disposed at this angle until it reaches the inner edge 36. The part of the inner channel surface 35 that extends the furthest in the third direction defines a crest, which is closer in the second direction to the portion of the inner channel surface 35 along the longitudinal portion 3 of the flow guide 2 than to the inner edge 36. In other words, a projection of the crest onto the transverse plane is closer to a line defined by the intersection of the inner channel surface 35 and the transverse plane than it is to the inner edge 36. The shape of the inner channel surface 35 encourages the fluid flow to attach to it as it turns due to the Coandă effect, which helps the fluid flow to turn smoothly and reduces the likelihood of turbulent flow.

Similarly, the outer channel surface 14 extends in the third direction from the longitudinal portion 3 of the flow guide 2 to the distal end portion 1 and passes through the transverse plane. It curves smoothly through an angle of more than 90° (in some embodiments, approximately 116°, more specifically, 116.4°) until it is disposed at the second angle towards the transverse plane. The remainder of the outer channel surface 14 defines an end portion of the outer channel surface 14 and remains at this angle until it reaches the outer edge 16. Thus, the channel 8 defines the chamber 42 between the transverse plane and an end portion of the channel 8 adjacent the outlet 10.

Referring to the longitudinal portion 3 of the flow guide 2, a longitudinal portion of the channel 8 runs parallel to a longitudinal axis of the laparoscope 6. The fluid flow travels through the longitudinal portion of the channel 8 along the laparoscope 6 in the third direction and then reaches the chamber 42. In the chamber 42, the fluid flow is made to turn through approximately 124° as it flows through the channel 8, as described above. As the fluid flow leaves the chamber 42 it enters the end portion of the channel 8. The cross-sectional flow area of the end portion of the channel 8 decreases between the chamber 42 and the outlet 10. This causes the flow speed of the fluid to increase again before it passes through the outlet 10.

The cross-sectional flow area of the portion of the channel 8 along the laparoscope 6 decreases from the inlet 5 to an entrance to the chamber 42. The entrance to the chamber 42, in turn, has a smaller cross-sectional flow area than the chamber 42 itself. This causes the fluid flow speed to increase as it approaches the chamber 42 and then decrease as it enters the chamber 42, which means it is travelling at a decreased speed when it turns in the chamber 42.

Thus, between the inlet 5 and the outlet 10, the flow speed increases up to the chamber 42, then decreases in the chamber 42 to facilitate a smooth change of flow direction and then speeds up again towards the outlet 10 for an increased exit speed. A smooth change of direction facilitated by the speed profile of flow through the flow guide 2 facilitates the choking point of the fluid flow to remain at the outlet 10, and therefore helps to maintain maximum speed of the fluid flow at the outlet 10. By ensuring a high speed at the outlet 10, in turn, the laparoscope 6 facilitates an improved flow attachment.

The outlet 10 is the locus of points beyond which the fluid flow is constrained only by the limb guide surfaces 20 and the surface 4 of the laparoscope 6. The outer limit of the outlet 10 is defined by the outer edge 16 of the outer channel surface 14. The inner limit of the outlet 10 is defined by a projection in the third direction of the outer edge 16 onto the end surface 4 of the laparoscope 6. All parts of the outer edge 16 of the outer channel surface 14 extend beyond the inner channel surface 35 in the second direction so that the inner limit of the outlet 10 is defined entirely by the end surface 4. In some embodiments, however, the central part of the outer edge 16 of the outer channel surface extends beyond the inner channel surface 35, but the parts of the outer edge 16 of the outer channel surface 14 adjacent each of the sides 12 of the channel 8 do not extend as far in the second direction as the inner channel surface 35. This causes the inner limit of the outlet 10 to be defined in part by the projection of the outer edge 16 onto the end surface 4 and in part by the projection of the outer edge 16 onto the inner channel surface 35.

In some embodiments, the flow guide 2 does not have the insert 37 or inner channel surface 35. The laparoscope 6 acts to define an equivalent of the inner channel surface 35 and, hence, the laparoscope 6 acts to define one side of the channel 8. These embodiments are now described with reference to FIGS. 8 to 10. It will be understood that the features of the above-described embodiments are equally applicable whether the insert 37 is present or not. In particular, regarding the features relating to the chamber 42, these apply to both kinds of embodiments, with an outer surface of the laparoscope 6 replacing, and acting as, the inner channel surface 35.

Figure 8:
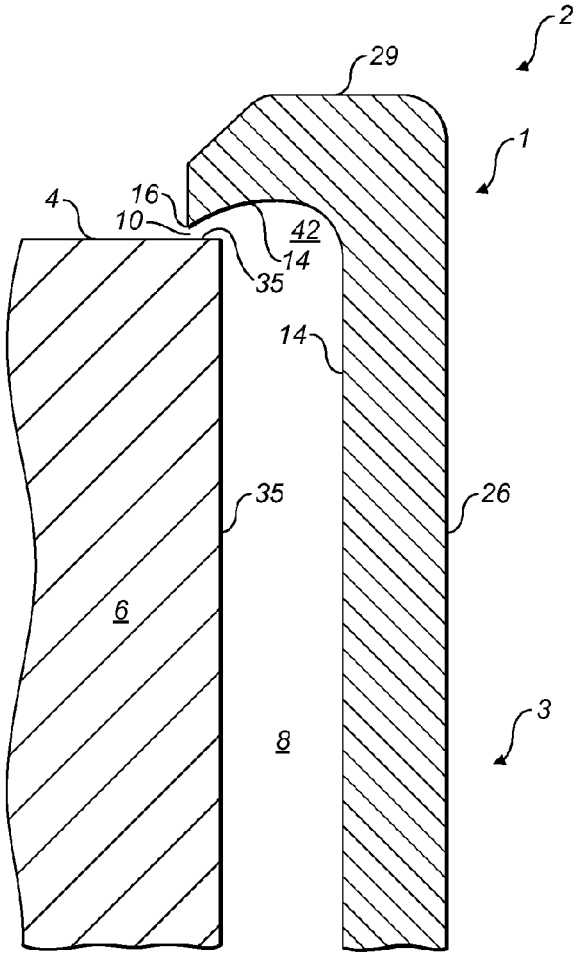
FIG. 8 depicts a cross-section of part of the distal end portion of the flow guide of other embodiments and part of the laparoscope when the flow guide is attached to the laparoscope.

With reference to FIG. 8, corresponding to FIG. 6, the chamber 42 is defined at the end portion of the channel 8 adjacent the outlet 10 and the outer channel surface 14 is curved at this portion. The insert 37 is absent, leaving the laparoscope 6 to define the inner channel surface 35. The absence of the insert 37 allows the longitudinal portion 3 of the flow guide 2 between the outer surface 26 and the outer channel surface 14 to be thicker without increasing the radius of the flow guide 2, thus increasing its strength.

Figure 9:
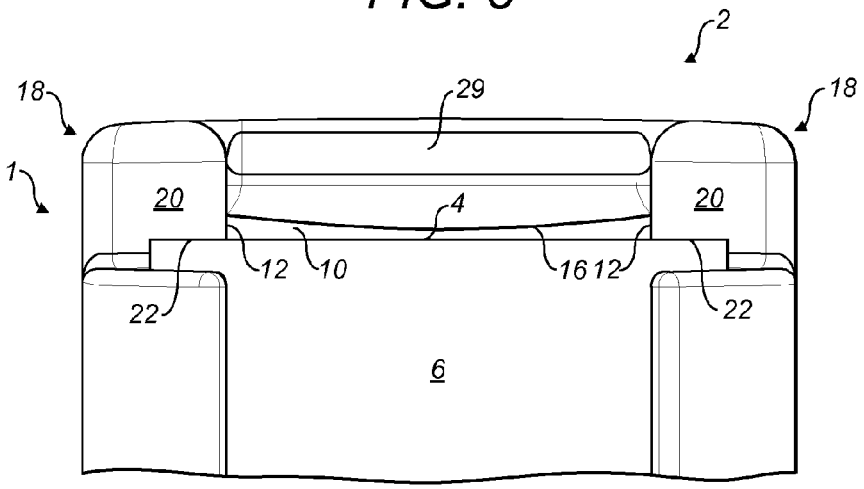
FIG. 9 depicts a side view of the distal end portion of the flow guide of these embodiments from the plane of the distal end surface of the laparoscope.

With reference to FIG. 9, which corresponds to FIG. 5, the absence of the insert 37 is visible just above and behind the laparascope 6.

Figure 10:
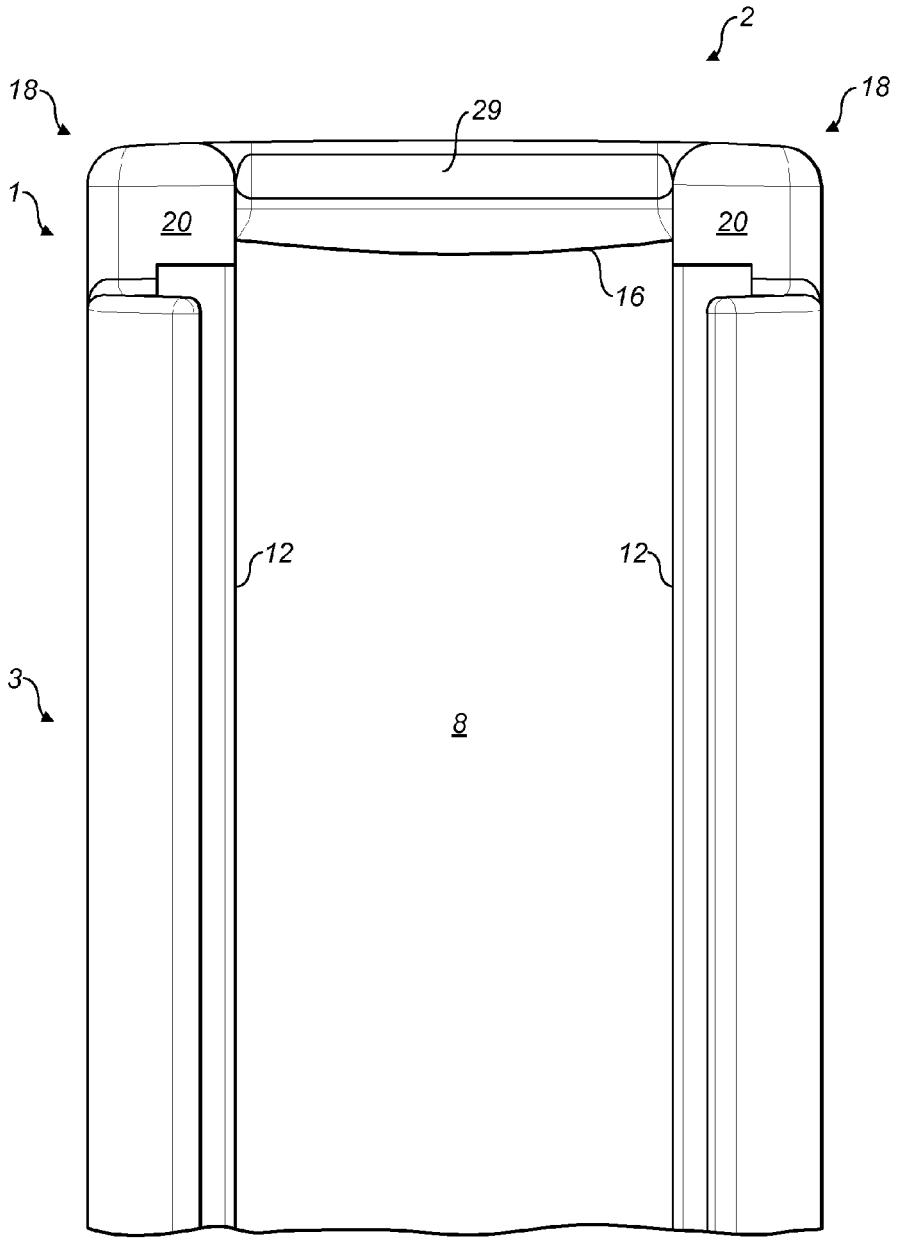
FIG. 10 depicts a side view of the distal end portion of the flow guide of these embodiments without the laparoscope.

With reference to FIG. 10, which corresponds to FIG. 7, the two sides 12 of the channel 8 are equidistant along the longitudinal portion 3 of the flow guide 2, thus making the cross-sectional flow area of the channel 8 constant, rather than varying, along this portion. The two sides 12 of the channel 8 are approximately 7 mm apart. The cross-section of the flow guide 2 itself is therefore also constant along this portion. The cross-sectional flow area of the channel 8 is approximately 4.5 $mm^2$, more specifically 4.53 $mm^2$. The outer edge 16 of the outer channel surface 14 is curved in a similar manner to the embodiment described with respect to FIG. 5. In some embodiments, however, the two sides 12 are arranged as described above to provide a varying cross-section. In some embodiments, the cross-section of the channel 8 along the longitudinal portion 3 varies, in spite of the absence of the insert 37, as described above in relation to FIG. 7.

Figure 11:
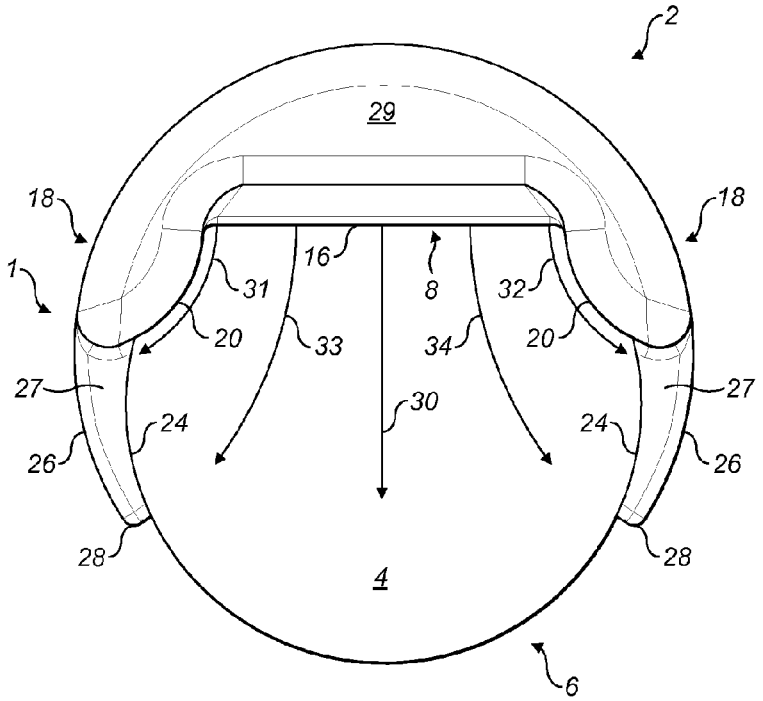
FIG. 11 depicts a face-on or top view of the distal end surface of the laparoscope with alternative embodiments of the flow guide attached to it.

With reference to FIG. 11, in some alternative embodiments, the embodiments described above are modified such that the outer edge 16 of the outer channel surface 14 is not curved in a plane defined by the first and second directions, so that the outer edge 16 of the outer channel surface 14 is in a plane defined by the first and third directions. This helps to create a parallel fluid flow through the outlet 10 in the second direction, so that the fluid flow does not begin to diverge until it begins to attach to the limb guide surfaces 20. The flow guide 2 is otherwise structured according to any of the embodiments described herein.

Figure 12:
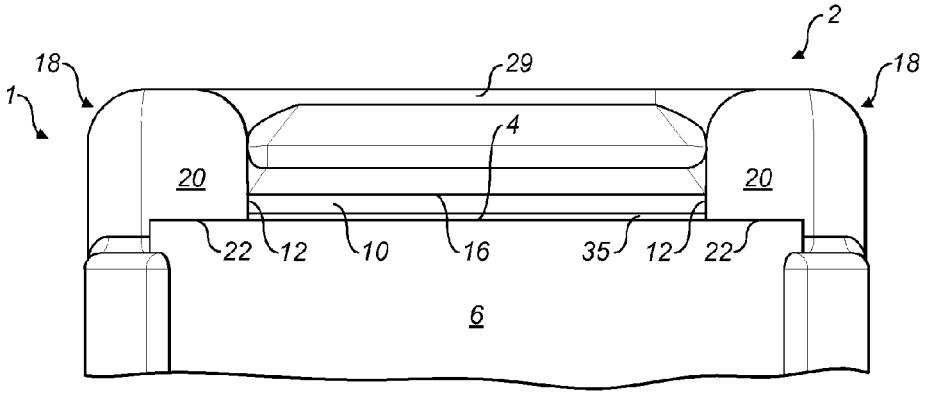
FIG. 12 depicts a side view of the distal end portion of other alternative embodiments of the flow guide from the plane of the distal end surface of the laparoscope.

With reference to FIG. 12, in some further alternative embodiments, the embodiments described above are modified such that the outer edge 16 of the outer channel surface 14 is not curved in a plane defined by the first and third directions, so that the outer edge 16 of the outer channel surface 14 is in a plane defined by the first and second directions. This ensures that all parts of the fluid flow are at a constant speed through the outlet 10 as the height of the outlet 10 in the third direction does not vary. The flow guide 2 is otherwise structured according to any of the embodiments described herein.

It will be understood that the above description of specific embodiments of the invention is by way of example only and it is not intended to limit the scope of the invention. Many modifications of the described embodiments, some of which are now described, are envisaged and intended to be covered by the appended claims.

In some embodiments, the outer surface 26 and the inner surface 24 do not meet at the tips 28 but both extend fully around the device. The outer surface 26 and the inner surface 24 are therefore substantially cylindrical and fully enclose the laparoscope. As described above, the channel 8 may be fully or partially formed on all sides by the flow guide 2 or one side may be fully or partially provided by the laparoscope 6. Various embodiments of fluid conduits for endoscopes are disclosed in UK patent application GB 0911891.0, from which PCT application PCT/GB2010/001302 claims priority, both of which are incorporated herein by reference.

In some embodiments, the portion of the channel 8 along the laparoscope 6, the chamber 42 and the portion of the channel 8 adjacent the limbs 18 combine to form a continuous surface.

In some embodiments, the flow guide 2 is made of any suitable known and approved medical plastic such as Radel A; Polyethersulfone; Radel R; Polyphenylsulfone and related/modified polymers; Polyetheretherketone (PEEK); Polyether Ketone Ketone (PEKK); Polyphenylene; Valox™ resins, for example based on Polyethyleneterephthalate (PET) or polybutyleneterephthalate (PBT); Polyethyleneterephthalate (PET); Polybutyleneterephthalate (PBT); Polycarbonates; Acrylonitrile Butadiene Btyrene (ABS); Polypropylene; Polyimides; and Polyacrylates. The flow guide 2 can also be manufactured, in some embodiments from metal, for example stainless steel metal (316L).

In some embodiments, the flow guide 2 is attachable to the laparoscope 6. In other embodiments, the flow guide 2 is integrally formed with the laparoscope 6. In some embodiments, the laparoscope 6 is a flexible or semi rigid endoscope, while in other embodiments, the laparoscope 6 is rigid.

In some embodiments, as the limb guide surfaces 20 extend from the sides 12 of the channel 8, they initially converge before they diverge as described above.

While the flow guide 2 described above is symmetrical about a plane defined by the second and third directions, which passes through the centre of the outlet 10, in other embodiments this is not the case.

In some embodiments, the fluid flow is a continuous flow, which creates a constant barrier protecting the end surface 4 from unwanted particles. In other embodiments, the fluid flow is a pulsed or intermittent flow, also of varying or stepped velocities, which is more effective in dislodging certain types of particles from the end surface 4.

In some embodiments, the first angle and the second angle are both the same, for example approximately 20°. In other embodiments, the first angle is approximately 0°, so that the portion of the inner channel surface 35 adjacent the limbs 18 is substantially in the transverse plane.

As described above, the outlet 10 is a single outlet. In other embodiments, the flow guide 2 provides a plurality of outlets.

In the embodiments described above, in the longitudinal portion 3 of the flow guide 2, the channel 8 defines a substantially straight path that is substantially parallel to the longitudinal axis of the laparoscope 6. However, in some embodiments, the channel 8 defines any curved or slanted path along the laparoscope 6, such as a helical path. The phrase 'longitudinally along' is intended to refer to any path with a component in the longitudinal direction. In some embodiments, the channel is arranged to direct the fluid flow in a curved or helical path across the end surface 4.

Although the specific description above has been made in terms of the flow guide 2 being attached to the laparoscope 6, it will be understood that the flow guide 2 can also be applied, with any necessary modifications, to cleaning a surface of any other device, in particular any optical surface of an optical device, more particularly a generally cylindrical device, for medical or non-medical uses. As well as for a laparoscope, some embodiments of the guide are suitable for use with other devices such as any other type of endoscope, scope or camera objective or any device with a surface that requires cleaning.

The above description is considered that of the preferred embodiment only. Modifications of the invention will occur to those skilled in the art and to those who make or use the invention. Therefore, it is understood that the embodiment shown in the drawings and described above is merely for illustrative purposes and not intended to limit the scope of the invention, which is defined by the following claims as interpreted according to the principles of patent law, including the doctrine of equivalents.

The invention claimed is:

1. A flow guide for directing a fluid flow across a surface of an endoscope, the flow guide comprising:

a locating arrangement for locating the endoscope with respect to the flow guide such that the surface of the endoscope is disposed generally in a first plane defined along first and second mutually perpendicular directions;

a channel for directing the fluid flow, the channel having sides spaced with respect to each other in the first direction and extending in a third direction perpendicular to the first and second directions;

an outer channel surface extending between the sides of the channel; and wherein an edge of the outer channel surface is convex-shaped to define an outlet of non-uniform height relative to the first plane, thereby imparting a non-uniform velocity profile to fluid constrained to flow between the edge of the outer channel surface and the first plane.

2. The flow guide of claim 1, wherein the edge of the outer channel surface is symmetrical about a third plane perpendicular to the first plane and a second plane defined by the first and third directions.

3. The flow guide of claim 1, wherein the edge of the outer channel surface is curved.

4. The flow guide of claim 1, wherein the outlet 10 is approximately 5.5 mm wide in the first direction.

5. The flow guide of claim 1, wherein the outlet is approximately 0.3 mm high in the third direction at the center of the outlet and approximately 0.7 mm high in the third direction at the sides of the outlet.

6. The flow guide of claim 1, wherein the edge of the outer channel surface forms an arc with a radius of approximately 9.5 mm.

7. The flow guide of claim 1, wherein the locating arrangement includes a base of a limb disposed generally in the first plane and arranged to rest against the surface of the endoscope.

8. The flow guide of claim 1, wherein the flow guide includes a respective limb extending from each of the sides generally in the second direction, each limb defining a limb guide surface extending generally in the third direction and being convex in a plane parallel to the first plane to cause fluid flow from the channel to diverge in the first direction as it flows across the surface of the endoscope.

9. The flow guide of claim 8, wherein the locating arrangement includes a base of the respective limb disposed generally in the first plane and arranged to rest against the surface of the endoscope so that the limb guide surfaces extend in the third direction from the surface of the endoscope.

10. The flow guide of claim 8, wherein each of the limb guide surfaces is generally curved in a plane defined by the first and second directions.

11. The flow guide of claim 1, wherein the edge of the outer channel surface is convex in a plane defined by the first and second directions.

12. The flow guide of claim 1, wherein the flow guide is arranged to direct the fluid flow at an angle of approximately 20° to the first plane.

13. The flow guide of claim 1, wherein the channel has an inner channel surface extending in the first direction between the sides of the channel, the inner channel surface generally facing the outer channel surface.

14. The flow guide of claim 13, wherein the inner channel surface is shaped to form a substantially continuous surface with the surface of the endoscope when the endoscope is secured to the flow guide.

15. The flow guide of claim 1, wherein the endoscope is substantially cylindrical and the surface of the endoscope is an end surface of the endoscope, wherein the flow guide is arranged to define a portion of the channel longitudinally along the endoscope for guiding the fluid flow longitudinally along the endoscope.

16. The flow guide of claim 15, wherein the channel comprises a chamber between the portion of the channel along the endoscope and a portion of the channel adjacent the edge of the outer channel surface, the chamber being shaped to turn the fluid flow from flowing along the endoscope to flowing across the end surface of the endoscope.

17. The flow guide of claim 16, wherein the chamber is shaped to turn the fluid flow through an angle of approximately 110°.

18. The flow guide of claim 16, wherein the chamber has a larger cross-sectional flow area than the portion of the channel adjacent the edge of the outer channel surface.

19. The flow guide of claim 16, wherein the cross-sectional flow area of the channel decreases from an inlet of the flow guide that is in fluidic communication with the channel to an entrance of the chamber.

20. The flow guide of claim 19, wherein the cross-sectional flow area of the chamber increases after the entrance.

21. The flow guide of claim 1, wherein the flow guide comprises an inlet in fluidic communication with the channel, the inlet having a larger cross-sectional flow area than the portion of the channel adjacent the edge of the outer channel surface.

22. The flow guide of claim 1, wherein the channel is continuous and has no internal obstructions to the fluid flow.

23. The flow guide of claim 1, wherein the flow guide is integrally formed with the endoscope or detachable from the endoscope.

24. The flow guide of claim 23, wherein the endoscope is substantially cylindrical and the surface of the endoscope is an end surface of the endoscope.

25. The flow guide of claim 23, wherein the surface of the endoscope includes a lens or optical window of the endoscope.

26. The flow guide of claim 23, in which the endoscope is a laparoscope.

*27. The flow guide of claim 25, wherein one of: the edge of the outer channel surface partially extends up to one of the lens and optical window of the endoscope; and the edge of the outer channel surface partially extends partially over one of the lens and optical window of the endoscope.*

*28. An endoscope comprising a transverse end surface including a lens or optical window and a flow guide as claimed in claim 1 for guiding a fluid flow longitudinally along the endoscope and directing the fluid flow across the transverse end surface of the endoscope, wherein the flow guide is integrally formed with the endoscope or detachable from the endoscope.*

* * * * *